United States Patent [19]
Dennison, Jr. et al.

[11] Patent Number: 5,205,280
[45] Date of Patent: Apr. 27, 1993

[54] QUICK-RELEASE ENDOSCOPIC COUPLING ASSEMBLY

[75] Inventors: Allan G. Dennison, Jr., Action, Mass.; Larry E. Shephard, Providence, R.I.

[73] Assignee: MP Video, Inc., Hopkinton, Mass.

[21] Appl. No.: 632,131

[22] Filed: Dec. 21, 1990

[51] Int. Cl.$^5$ .................................................. A61B 1/00
[52] U.S. Cl. .......................................... 128/3; 128/4; 358/98; 403/DIG. 4
[58] Field of Search .................. 128/3, 4, 852, 5, 6-9; 358/98, 93, 83; 403/DIG. 4; 285/85, 81

[56] References Cited

U.S. PATENT DOCUMENTS

| | | | |
|---|---|---|---|
| 3,583,731 | 6/1971 | Jewell | 285/85 |
| 4,182,558 | 1/1980 | Matsuo | 403/DIG. 9 X |
| 4,305,386 | 12/1981 | Tawara | 128/4 |
| 4,318,395 | 3/1982 | Tawara | 128/4 |
| 4,323,304 | 4/1982 | Ishii | 354/62 |
| 4,369,767 | 1/1983 | Shishido | 128/6 |
| 4,413,278 | 11/1983 | Feinbloom | 358/93 |
| 4,426,063 | 1/1984 | Bormioli | 251/149.9 |
| 4,440,157 | 4/1984 | Shishido | 128/6 |
| 4,552,131 | 11/1985 | Omagari | 128/6 |
| 4,611,888 | 9/1986 | Prenovitz et al. | 350/96.22 |
| 4,722,000 | 1/1988 | Chatenever | 358/98 |
| 4,781,448 | 11/1988 | Chatenever et al. | 350/429 |
| 4,807,594 | 1/1989 | Chatenever | 128/4 |
| 4,903,710 | 2/1990 | Jessamine et al. | 128/852 X |

OTHER PUBLICATIONS

Advertisement Karl Storz, "Supercam Puts the Power of Documentation At Your Fingertips".
Advertisement of Edwards Orthopaedics, "Seeing is Believing"; Baxter Healthcare Corporation, 1988.
Advertisement from Stryker Endoscopy; "The Gold Standard", Oct. 1988.
Advertisement entitled "Focus on Reliability"; 1987; Zimmer.
Advertisement of Concept Incorporated; entitled "Arthroscopy", Intravision Camera and Coupler.
Advertising brochure Precision Optics Corporation; "Image Couplers".
Brochure from Aesculap; "Aesculap Arthroscopy System".
Advertisement from Arthromed Color TV System.
An Advertising Flyer from Stryker Surgical; "570 CCD Plus Medical Video Camera".
Article from Bi-Medical Engineering; entitled "Miniature Black and White TV Camera for Endoscopy and Other Medical Applications"; George Berci, et al.; Apr. 1972.

Primary Examiner—Robert A. Hafer
Assistant Examiner—Sam Rimell
Attorney, Agent, or Firm—Frost & Jacobs

[57] ABSTRACT

There is provided a quick-release coupling assembly for an endoscopic ocular, the assembly including an ocular mounting surface having an aperture and a longitudinal axis preferably passing through the center of the aperture on the mounting surface. A stationary guidewall is preferably radially spaced from and substantially concentric with the aperture of the ocular mounting surface, and the guidewall at least partially encircles the aperture to define an alignment recess adjacent the mounting surface for receiving the proximal end of an endoscopic ocular. At least one gripping jaw is provided for axial reciprocation and having a clamping position and a release position. The jaw comprises an inner tab which extends outwardly from the mounting surface, a retainer flange extending radially inwardly, and an engagement surface which may preferably be angularly disposed relative the axis. When reciprocated to the release position, the engagement surface is outside of the alignment recess, and when reciprocated to the clamping position, it can engage a portion of the proximal end of an ocular eyepiece positioned within the alignment recess. In a preferred embodiment, the assembly includes a pair of oppositely disposed gripping jaws for releasably engaging the proximal end of an ocular to be coupled. The engagement surface of the jaw may also include a tapered lip to readily accommodate ocular eyepieces of various sizes and shapes.

21 Claims, 6 Drawing Sheets

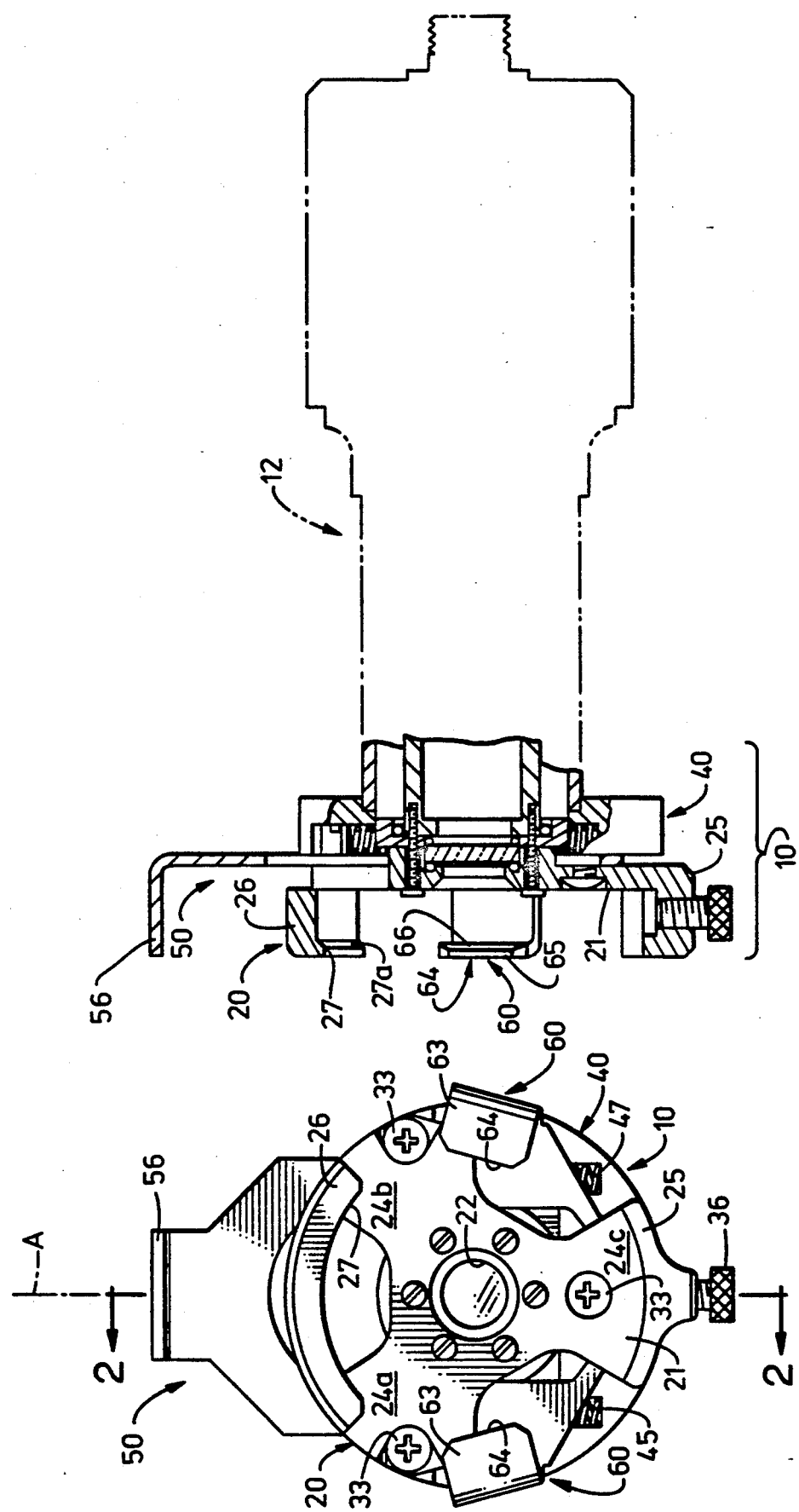

QUICK-RELEASE ENDOSCOPIC COUPLING ASSEMBLY

TECHNICAL FIELD

This invention relates to a mechanism for releasably grasping an endoscope which is to be coupled to a video camera device for medical procedures and the like, and, more particularly, to an improved quick-release endoscopic coupling assembly featuring a substantially open and unobstructed arrangement to facilitate attachment procedures and maintenance.

BACKGROUND ART

The use of endoscopic instruments and the adaption of video camera technology to endoscopic imaging has proven to be quite advantageous in a wide variety of surgical procedures and general diagnostic applications. Typically, an endoscopic instrument includes an elongated probe for use in penetrating and viewing remote and otherwise inaccessible body regions. Various endoscopic devices and surgical techniques have enabled the simplification of many surgical operations, and examples of commonly used endoscopic instruments include the laparascope, cystoscope, arthroscope, bronchoscope, and the colonoscope, whose names are obviously indicative of their functions and anatomical areas of use.

Conventional endoscopic systems include an endoscope, an optical adapter and a video camera head. Before each use, the endoscopic system must be adequately cleaned and sterilized, such as by soaking or immersion in a sterilizing or disinfecting solution and/or sterilization by use of ethylene oxide gas. Conventional endoscopic devices required the surgeon to view the target area directly through the eyepiece of the endoscope, which typically necessitated the surgeon bending over or otherwise situating himself in awkward positions so as to be able to view through the eyepiece. Video camera technology has been adapted to overcome these kind of inconveniences, and a typical assembly for adapting such camera technology to an endoscope includes a mechanism for grasping the endoscopic eyepiece and coupling the same to the camera head or similar equipment. The coupling device generally has a fitting at its proximal end which attaches to the video camera or an adapter unit attached to the camera head. The distal end of the coupler comprises the mechanism for grasping the endoscopic eyepiece. Often the adapter unit includes adjustable viewing optics for the video camera to provide for focusing, zoom characteristics and the like.

In addition to the need for disassembling the endoscope from the camera head and/or adapter for cleaning procedures between uses, many surgical and diagnostic procedures require the interchangeability of endoscopes during the procedure. To facilitate such interchangeability, it is preferred that the coupling mechanism be of a "quick-release" variety which is simple in operation and reliable. Because time is generally of the essence during these procedures, and with the procedures generally being of a delicate nature, the coupling mechanism must be of a relatively simple design which is easy for doctors and surgical assistants to use.

A variety of mechanisms have been implemented in the industry for releasably attaching an endoscope to a video camera head. For example, U.S. Pat. No. 4,807,594, which issued to D. Chatenever on Feb. 8, 1989 teaches the substitution of the typical eyepiece of an endoscope with a collar rotatably secured by threaded connections to a focusing adapter which is, in turn, connected to the camera head. Such arrangement thereby eliminated the eyecup of a scope and provided direct attachment of the endoscope to the camera body while allowing relative rotation therebetween. Use of this system, however, limits the interchangeability of the endoscope to particular parts designed for that adapter.

An alternative attachment arrangement shown in U.S. Pat. No. 4,369,767, which issued to Y. Shishido on Jan. 25, 1983, illustrates a radial set screw type arrangement. However, these rotatable and set screw type coupling arrangements fail to provide the relatively quick attachment/release most preferably desired in these endoscopic devices. Additionally, users of endoscopic instruments often require that the endoscope be rotatable independently of the camera head. The threaded and set screw type arrangements do not generally provide for such independent rotation.

Bayonet-type arrangements have also been widely utilized in the endoscopic device industry, as generally shown in U.S. Pat. No. 4,323,304, which issued to F. Ishii on Apr. 6, 1982. The Ishii ocular section of endoscope is attached to a photographic camera via a plurality of bayonet pawls which radially project from the inner periphery of the connection opening. The general problem with bayonet-type locking arrangements is that they do not permit independent rotation of the endoscope relative to the camera adapter unit. U.S. Pat. No. 4,611,888, which issued to M. Prenovitz et al. on Sep. 16, 1986, discloses an improved bayonet-type, quick-release coupling arrangement which can be detached by merely a slight twist, and which includes front and rear sections which are rotatable relative one to another in order to provide rotation of the endoscope relative to the camera head, as desired. This arrangement, however, requires the replacement of the endoscopic eyepiece with a threaded collar/adapter ring arrangement. While a quick-release, rotatable assembly is provided, the modification of the endoscope eyepiece required is not always feasible and/or convenient.

U.S. Pat. No. 4,781,448, which issued to D. Chatenever et al. on Nov. 1, 1988, describes a zoom lens adapter for an endoscopic camera which includes a gripping mechanism comprising a plurality of projecting tines for removably engaging the eyecup of an endoscope. While additional details of the projecting tines of this reference are not provided, FIG. 2 of the patent illustrates a cup-shaped grasping mechanism having a circular central aperture within which the eyepiece of the endoscope is apparently inserted for grasping by the radial tines. Because of the inherent need to thoroughly clean and disinfect these devices between uses, the substantially enclosed cup-like characteristics of this grasping mechanism and its radially moveable tines cause increased difficulty in accomplishing cleaning and maintenance of the device, and can allow moisture to collect and interfere with optimal use of these devices. For example, such moisture can condense and fog the optics in use. Furthermore, such structure does not provide a relatively clear view of the coupling mechanism in use to assure that the scope is firmly locked in place and to avoid accidental disconnection and damage which can result therefrom.

Similar mounting devices or endoscopic eyepieces are shown in U.S. Pat. Nos. 4,305,386 and 4,318,395 which issued to I. Tawara. These references discuss the shortcomings of the bayonet-type and friction-type mounting devices commonly available in the industry, specifying that such devices lack the ability to provide immovable and rotatable connection of the ocular device. The Tawara mounting devices utilize one or more swingable or rockable cams which are normally biased inwardly by tension springs, whereby an ocular device may be snapped into the inner portions of an inwardly tapered conical cavity. Immovable clamping can be obtained by rotation of a fixing cam ring, and release of the eyepiece can be obtained by appropriate rotation of a release cam ring. These systems are relatively complicated in their use of a plurality of cams, springs, and rotatable rings. Additionally, the requirement of an inwardly tapered conical cavity makes cleaning and maintenance more difficult, and substantially obstructs the view of the user during actual use of the device.

An expanding-type coupling apparatus is shown in U.S. Pat. No. 4,413,278, which issued to R. Feinbloom on Nov. 1, 1983. The Feinbloom device includes two semi-circular arms which are pivotally attached at their lower ends and biased by a pair of springs at their upper ends. These opposed C-shaped arms are mounted within an aperture formed in a front cover, and can be moved radially to enable the placement or removal of the front section of an arthroscope therewithin. Again, this arrangement does not provide for convenient cleaning and/or maintenance, and does not provide for substantially unencumbered viewing of the coupling mechanism in use.

Most recently, there are a variety of coupling mechanisms available in the industry from companies such as Stryker and Zimmer which comprise an elongated, unitary ring-like element located between an outer cover member and an inner alignment surface for an endoscopic eyepiece. The ring-like device includes a tapered clamping surface which is spaced from the alignment surface to accommodate the thickness of the eyepiece, and is normally urged into an engagement position with an eyepiece located within the coupler. The ring-like member can be axially reciprocated to move the clamping portion out of engagement with the eyepiece for release. Again, however, these ring-like coupling mechanisms are quite similar to the Feinbloom mechanism in that they do not substantially address the problems of facilitating ease of cleaning and maintenance, and do not provide a compact coupling mechanism of substantially open character which permits relatively unencumbered viewing of the coupling mechanism in use to facilitate attachment and release procedures and enhances air circulation to obviate collection of moisture. Additionally, the spacing of the ring-like member from the alignment surface adds size and bulk to the assembly.

As a result, heretofore, there has not been available in the industry a relatively simple and compact, easy-to-use endoscopic coupling mechanism which is substantially open at its distal end for simplified manufacture, use, maintenance and cleanup. While various quick-release mechanisms have become available in the industry, none permit substantially unrestricted access to the eyepiece mounting surface in use, while providing a simplified operating mechanism which will not only facilitate the attachment and replacement of various endoscopic eyepieces by a surgeon or technician, but will further simplify and prove the efficiency of cleaning procedures, sterilization, maintenance, antifogging, and verification of secure attachment.

DISCLOSURE OF THE INVENTION

It is an object of this invention to obviate the above-described problems and shortcomings of the endoscopic coupling mechanisms heretofore available in the industry.

It is another object of the present invention to provide an improved quick-release coupling mechanism for endoscopic devices which is simple in structure, compact, easy to use, reliable, and facilitates implementation of quick attachment or release of endoscopes in use.

It is yet another object of the present invention to provide a compact quick-release coupling mechanism for endoscopic devices which is substantially open in nature to provide relatively unencumbered visual access to the coupling structure in use, which facilitates cleaning, maintenance and sterilization procedures and which insures a secure fitting of the eyecup to the coupling mechanism in use.

It is also an object of the present invention to provide a quick-release endoscopic coupling mechanism which is simple and reliable in use, and which can be adapted to permit rotation of the endoscope relative the coupling mechanism or, alternatively, to prevent rotation of the endoscope relative the coupling mechanism, as desired.

In accordance with one aspect of the present invention, there is provided a quick-release coupling assembly for releasably connecting an endoscopic ocular having proximal and distal ends, with the assembly including an ocular mounting surface having an aperture and a longitudinal axis passing through the center of the aperture. Semi-circular stationary guidewall is preferably radially spaced from and substantially concentric with the aperture of the ocular mounting surface, and the guidewall at least partially encircles the aperture to define an alignment recess adjacent the mounting surface for receiving the proximal end of an endoscopic ocular. At least one gripping jaw is provided for reciprocation along the longitudinal axis, having a clamping position and a release position. The jaw comprises an engagement surface which extends outwardly from the mounting surface and, in a preferred embodiment, is angularly disposed relative the longitudinal axis. The jaw further comprises a retainer flange attached to the engagement surface and extending radially inwardly so that when reciprocated to the release position, the jaw is longitudinally moved substantially outside of the alignment recess. When reciprocated to the clamping position, the jaw engages a portion of the proximal end of an ocular positioned within the alignment recess to effectively clamp the ocular within the recess. In a preferred embodiment, the assembly includes a pair of oppositely disposed gripping jaws for releasably engaging the proximal end of an ocular to be coupled.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 1 is a front elevational view of a quick-release endoscopic coupling assembly made in accordance with the present invention;

FIG. 2 is a partial cross-sectional view of the coupling assembly shown in FIG. 1, illustrated from a side elevational orientation and shown attached to the distal end of an endoscopic adapter device;

DETAILED DESCRIPTION OF THE INVENTION

Figure 3A:
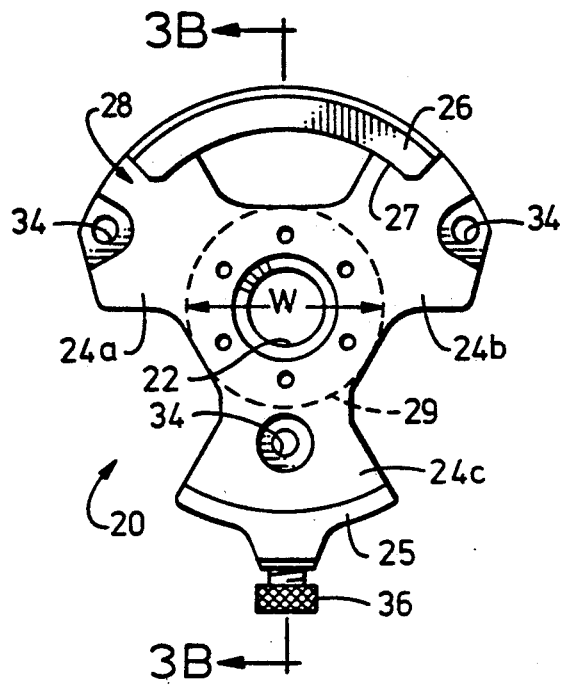
FIG. 3A is a front elevational view of the coupler seat element of a quick-release endoscopic coupling assembly as shown in FIGS. 1 and 2.

Referring now to the drawings in detail, wherein like numerals indicate the same elements throughout the views, FIGS. 1 and 2 illustrate a preferred embodiment of a quick-release endoscopic coupling assembly 10 made in accordance with the present invention. FIG. 2 shows a partially broken out sectional view for clarity, illustrating coupling assembly 10 as it might preferably be attached to an endoscopic focusing device or adapter 12. Details of the focusing device/adapter 12 have been omitted as not pertinent to the present invention and well known in the industry. FIGS. 3A, 3B, 4A, 4B and 5 show additional details of the various elements of coupling assembly 10 and its preferred mounting on an endoscopic focusing device or adapter 12.

Figure 3B:
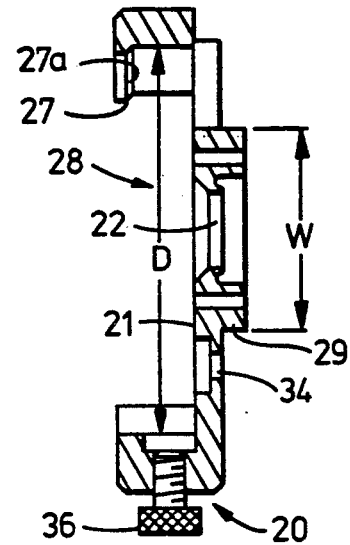
FIG. 3B is a vertical cross-sectional view of the coupler seat of FIG. 3A, taken along lines 3B—3B thereof.

In particular, FIGS. 1 and 2 show a coupling assembly 10 comprising a coupler seat 20 attached to a coupler retainer 40, between which is reciprocably mounted coupler blade 50. As best seen in FIGS. 1, 3A and 3B, coupler seat 20 provides a relatively planar ocular mounting surface 21 having an aperture 22 formed therethrough for alignment with camera focusing optics such as will often be included within an adapter 12. For reference, a longitudinal axis A is shown as passing through the center of aperture 22 of coupler seat 20, as illustrated in FIG. 1. As will be understood, it is not critical that axis A pass through the center of seat 20.

As seen best in FIG. 3B, preferably extending rearwardly from ocular mounting surface 21 about the periphery of aperture 22 is spacer 29 for providing a predetermined mounting space between seat 20 and retainer 40 within which the longitudinally reciprocable coupler blade 50 can be slidably retained.

Figure 5:
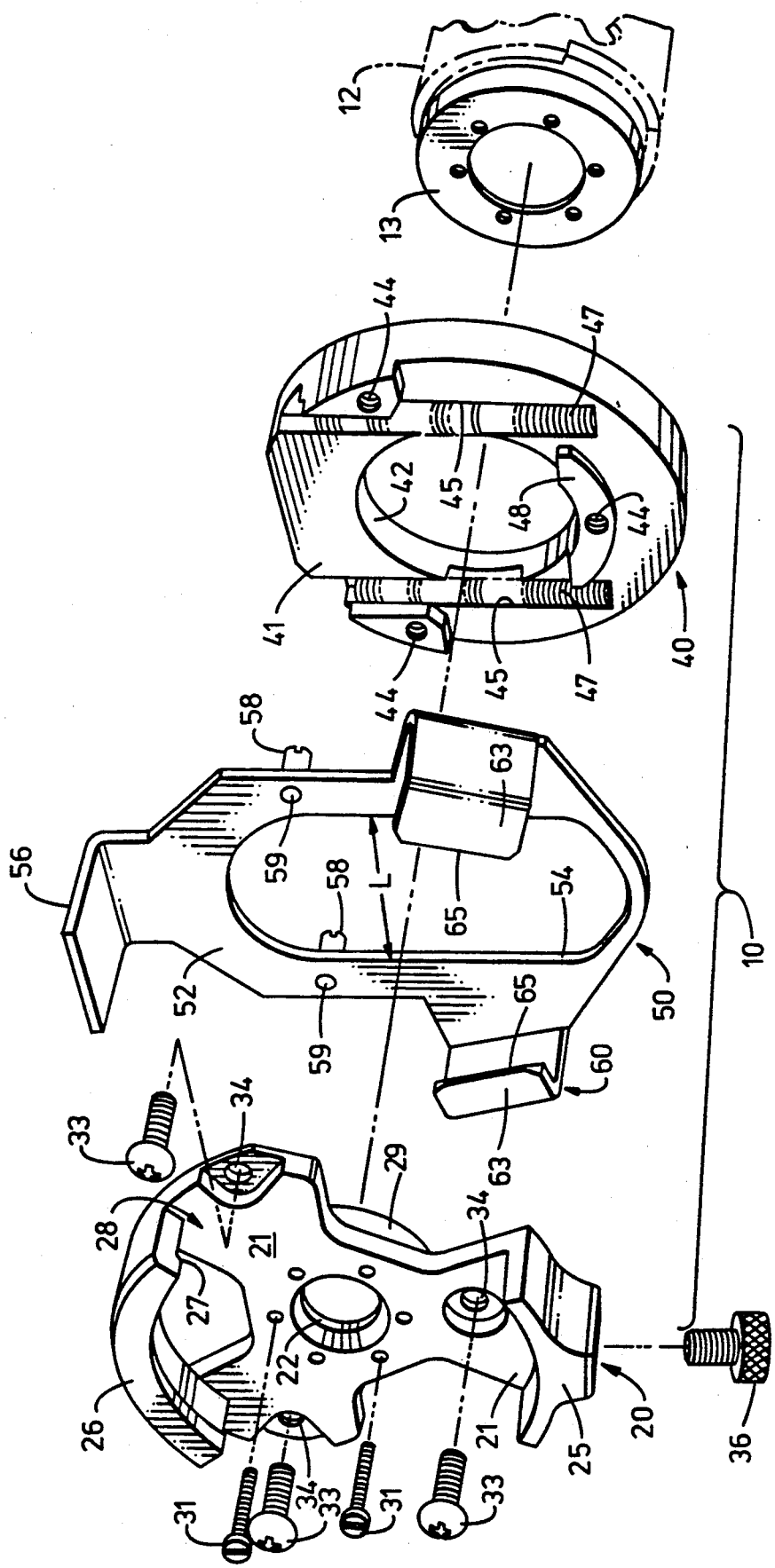
FIG. 5 is a partial, exploded assembly view of the quick-release endoscopic coupling assembly as shown in FIG. 2.

As seen best in FIG. 5, it is contemplated that coupling assembly 10 can be conveniently mounted to the distal end 13 of an endoscopic adapter or focusing device 12 by any convenient means such as a plurality of screws 31 which extend through corresponding bores in coupler seat 20 and are threadedly received in end 13. Coupler seat 20 is also preferably attached to retainer 40 in order to maintain coupling assembly 10 as a unit, such as by a number of screws 33 threadedly received in bores 44 of retainer 40. Coupling assembly 10 can then be attached to an endoscopic device via screws 31, as described.

Extending outwardly from ocular mounting surface 21 is at least one semi-circular stationary guidewall 26 radially spaced from aperture 22. Because typical endoscopic eyepieces (such as generically shown at 15 of FIG. 6) comprise a substantially disk-like or rounded proximal end (e.g. end 16 shown in FIG. 6) having a circular flange (e.g. 17), it is preferred that guidewall 26 feature a generally semi-circular conformation as illustrated.

It is also preferred that a plurality of stationary guidewalls (e.g. 25 and 26) be provided in a semi-circular arrangement in conjunction with mounting surface 21 to at least partially encircle aperture 22 and to define an alignment recess 28 adjacent mounting surface 21 for receiving the proximal end (e.g. 16) of an endoscopic ocular. Any number of guidewall structures could equally be utilized to provide an alignment recess 28, which preferably functions to at least generally and preliminarily align the eyepiece of an endoscope with aperture 22 and the balance of any attached video camera optics. As will be understood, it is also preferred that one or more of the guidewall structures, (e.g. 26) include a retention lip 27 for retaining the eyepiece of an endoscope in close proximity with ocular mounting surface 21 in use. As illustrated, retention lip 27 can preferably comprise a slightly tapered inner or recessed edge 27a.

It should also be noted that coupler seat 20 comprises an overall skeletal or open structure including a plurality of spoke-like structures 24a–24c radiating from adjacent aperture 22. Spokes 24a–24c are preferably substantially planar in nature to facilitate provision of the substantially planar mounting surface 21, while also providing a open overall structure to coupling assembly 10 which can be more easily cleaned and maintained. The spokes also help provide a secure coupling ability while facilitating air circulation around and through assembly 10 to prevent collection of moisture which can fog the optics of the endoscope.

Coupler retainer 40 also comprises an aperture 42 corresponding with and generally aligned with aperture 22 and the video camera optics which may be provided within focusing device 12.

Figure 4A:
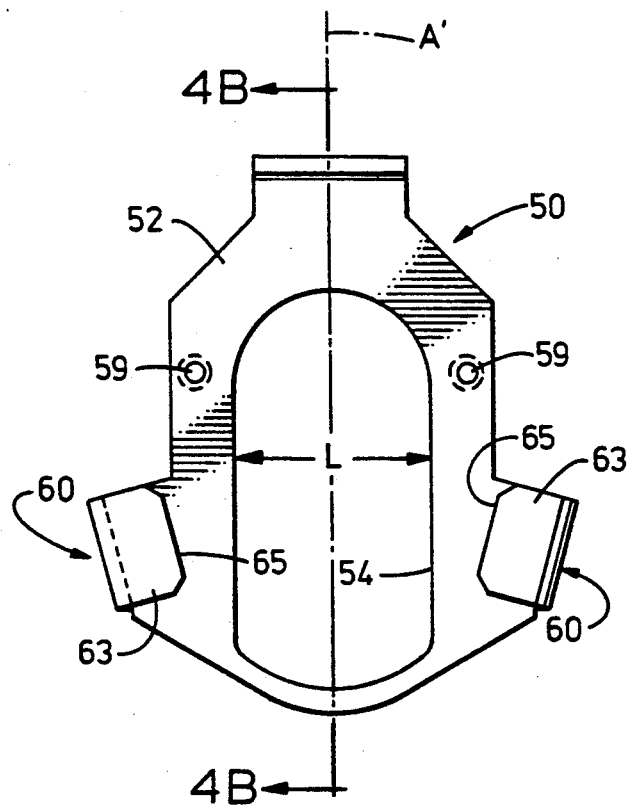
FIG. 4A is a front elevational view of a preferred coupler blade of a quick-release endoscopic coupling assembly as shown in FIGS. 1 and 2.
Figure 4B:
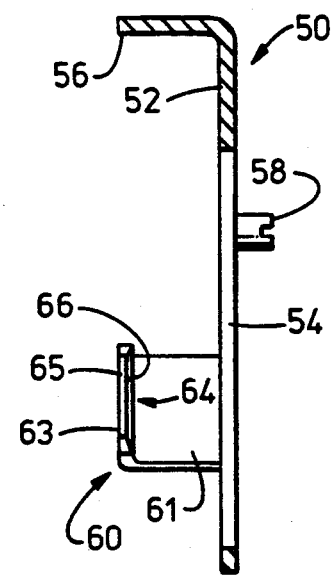
FIG. 4B is a vertical cross-sectional view of the coupler blade of FIG. 4a, taken along line 4B—4B thereof.

Sandwiched between coupler seat 20 and retainer 40 is coupler blade 50, preferably featuring a substantially ribbon-like or blade-like body 52 with a centrally located slot 54 for captively mounting blade 50 on spacer 29 while permitting longitudinal movement relative thereto. As best seen in FIGS. 4A, 4B and 5, coupler blade 50 is preferably integrally formed from a single flat piece of material such as stainless steel or the like, and includes an upwardly and forwardly oriented blade actuation flange 56 adjacent the lower portions of its body 52. Slot 54 is designed with a predetermined lateral dimension L corresponding with the outer dimension or width W of spacer 29 of coupler seat 20. As seen best in FIG. 5, coupler retainer 40 preferably comprises a coupler blade slot guide 48 having a lateral dimension corresponding to dimension L to further provide alignment and lateral support for blade 50 as it is reciprocated, and to provide a limit or stop for longitudinal movement of blade 50 toward its upper or engaged position, as will be discussed below.

Blade 50 further comprises at least one gripping jaw 60 which includes an inner surface or tab 61. Formed along the distal edge of the outwardly extending tab 61 is a retainer flange 63 which extends radially inwardly as shown. An engagement surface or lip 64 is provided along the innermost portions of flange 63, and lip 64 is preferably angularly disposed relative the axis (A') of blade 50 as illustrated. In a preferred embodiment, a pair of gripping jaws 60 are provided in symmetrically opposed relation, such as the ten o'clock-two o'clock positions illustrated in FIG. 4A.

Figure 6:
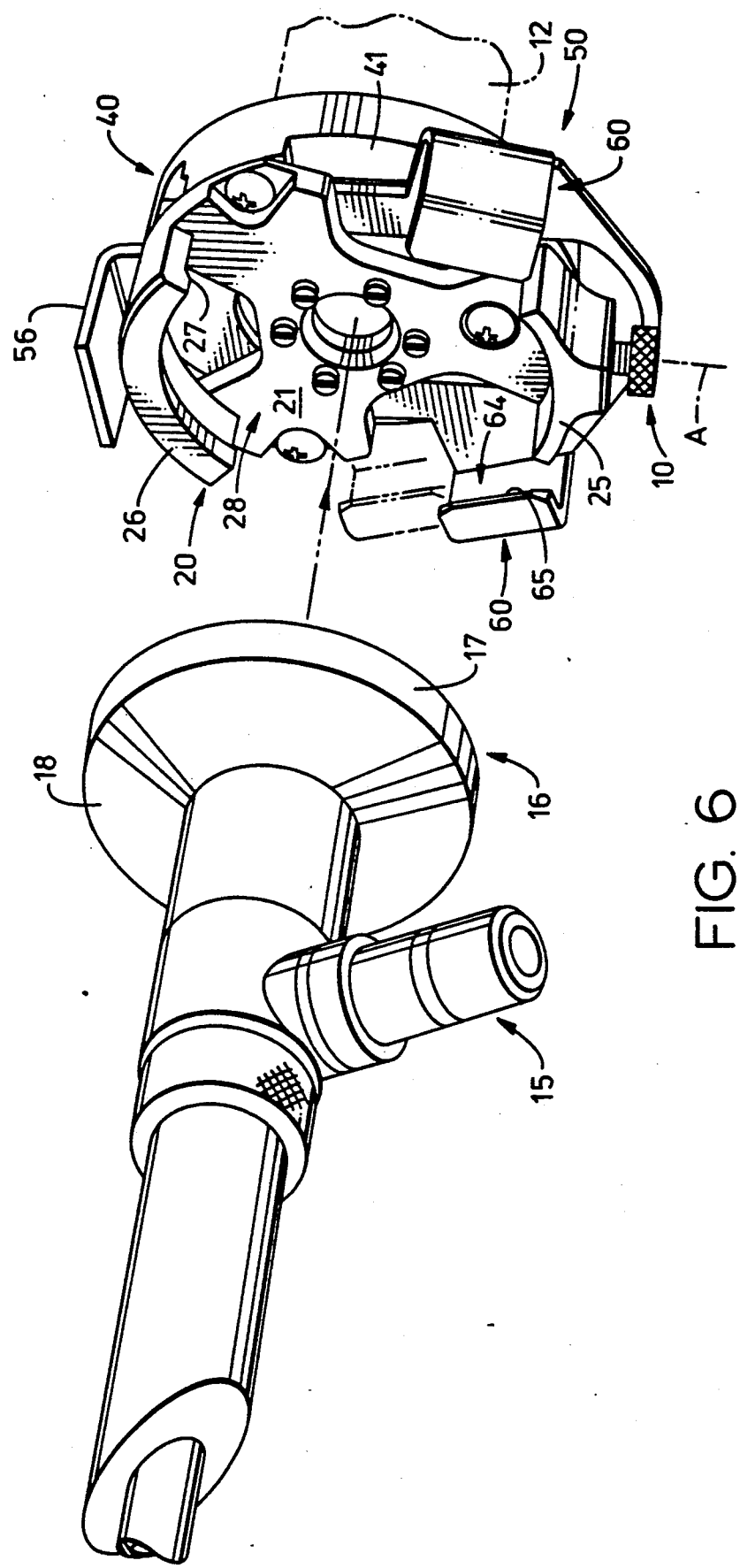
FIG. 6 is a partial perspective view illustrating the coupling/release operation of a quick-release endoscopic coupling assembly made in accordance herewith, with the coupling assembly shown with its gripping jaws in release position.
Figure 7:
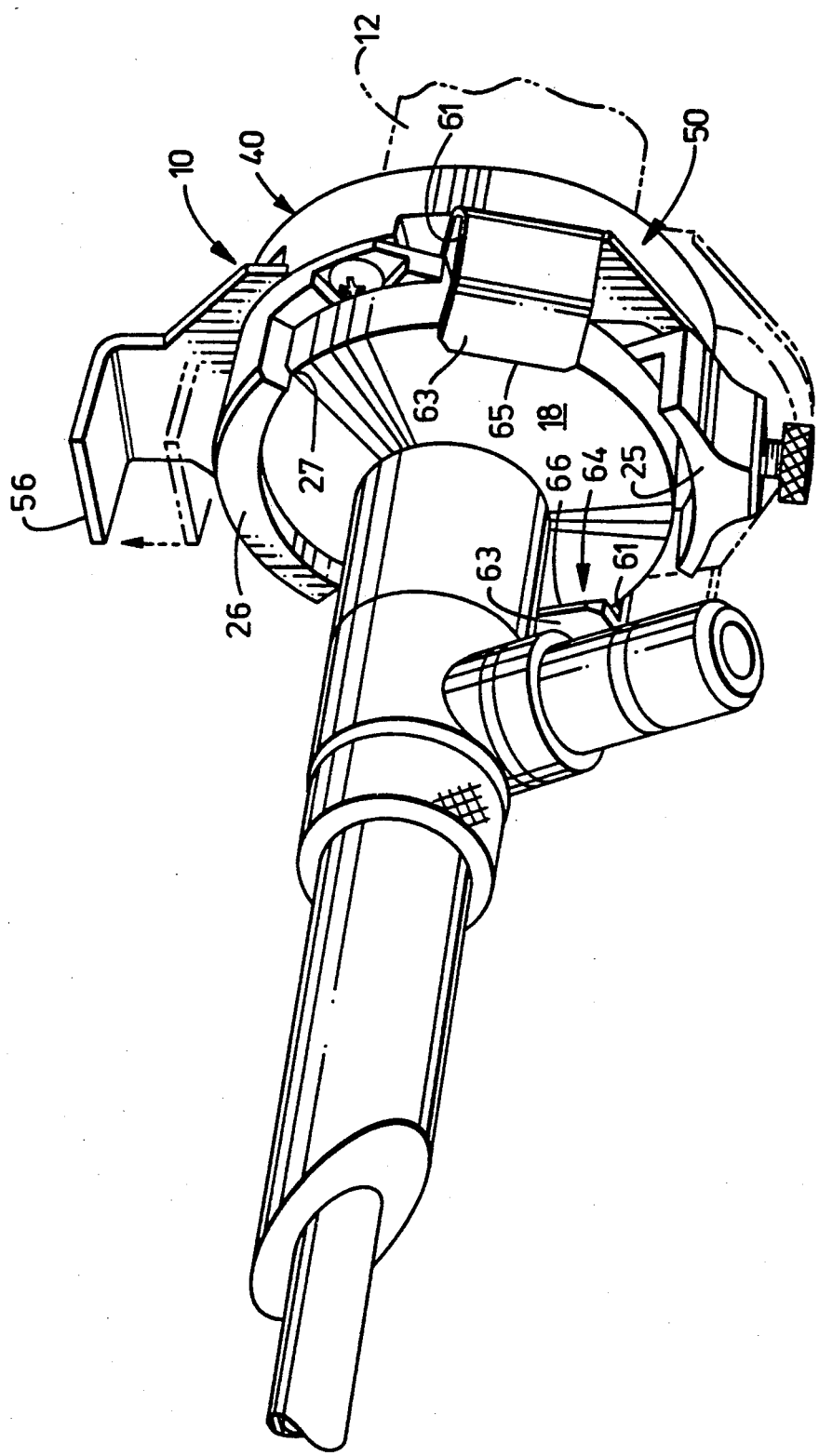
FIG. 7 is a partial perspective view similar to FIG. 6, showing the quick-release assembly in engagement position with an endoscopic ocular.

FIG. 4B shows a side elevational view of coupler blade 50, and best illustrates the outwardly extending nature of inner surface or tab 61. FIG. 4B also illustrates the tapered lip 66 of engagement surface 64 for engaging a variety of endoscopic eyepieces. Particularly, engagement surface or lip 64 has a radially inwardmost distal surface or tip 65 where the thickness of engagement lip 64 is thinnest, from which lip 64 extends along tapered surface 66 in a radially outward direction as shown. In conjunction with the angled orientation of lip 64 relative axis A' of blade 50, this tapered feature enables gripping jaws 60 to firmly grasp a virtually unlimited assortment of endoscopic oculars of eyecups 15 (as illustrated in FIGS. 6 and 7) without a need for manual adjustments. As will be appreciated, eyecups available in the industry having varying outside diameters (i.e. of circular flanges 17), angles of taper of their conical rear faces (i.e. face 18), and thicknesses of the circular flanges (i.e. 17). The tapered nature of lips 64 of the gripping jaws 60 helps accommodate these inherent variations with a single structure. Angular orientation of jaws 60 relative axis A' may also facilitate the accommodation of eyecup variations as well.

FIG. 4B illustrates a rearwardly extending biasing tang 58 which is provided as a preferred means for providing a biasing force to coupler blade tending to move blade 50 into its engagement position. In particular, as seen in FIG. 5, blade 50 is preferably mounted such that spacer 29 of coupler seat 20 extends through slot 54 to captively sandwich coupler blade 50 between seat 20 and retainer 40. Due to the skeletal structure and spoke-like configuration of seat 20, gripping jaws 60 extend outwardly past seat 20 and outwardly from its mounting surface 21 without interference. As can be appreciated, the elongated nature of slot 54 allows for axial reciprocation of coupler blade 50 relative seat 20 and retainer 40 along the central axes A and A' (which are at least parallel to one another in assembled condition, and are preferably substantially coaxial). The corresponding lateral dimension L of slot 54 and the outer dimension or width W of spacer 29 should be so sized to allow substantially unencumbered axial movement of blade 50 relative to seat 20, while providing substantial stability and guidance to maintain coupler blade 50 in a predetermined relationship with seat 20.

In a preferred embodiment, coupler blade 50 further comprises one or more rearwardly extending biasing tangs 58 designed to interact with one or more compression springs 47 provided within complimentary spring enclosures 45 formed in coupler retainer 40. While any means for biasing coupler blade 50 toward a predetermined position can equally be utilized, the recessed spring enclosures 45 and rearwardly extending biasing tangs 58 are preferred to provide additional stability to coupler blade 50 as it is axially reciprocated within coupling assembly 10. Biasing tangs 58 can preferably comprise small knobs screwed into blade 50, or can be integrally formed, such as by a punching process, with the planar sheet material from which blade 50 is provided. In fact, it is contemplated that coupler blade 50 can be preformed from a single blank of lightweight material by a combination of punching, bending, and/or other common machining processes.

The generally open or skeletal overall characteristics of both coupler blade 50 and coupler seat 20 are preferred to facilitate drainage of liquids, and improved air circulation to help avoid undesired fogging of associated camera lenses as moisture evaporates between them. The ribbon-like or blade-like nature of coupler blade 50 also enables blade 50 to be reciprocable in close proximity to seat 20 while minimizing the overall size of coupling assembly 10. As illustrated and described, in a preferred arrangement, blade 50 can be reciprocable on seat 20 and along mounting surface 21 without adding significantly to the thickness or size of assembly 10, unlike prior art gripping devices which required spacing a reciprocable member from the mounting surface to accommodate the thickness of the occular itself.

Biasing tangs 58 are preferably sized to nicely fit within spring enclosures 45, whereby a predetermined amount of biasing force can be provided to coupler blade 50 to maintain blade 50 and its gripping jaws 60 in an engagement position, as illustrated in FIG. 1. Biasing tangs 58 may preferably be provided as cylindrical nobs which can be threadedly received into corresponding threaded bores (e.g. 59) in blade 50.

When coupler blade 50 is pushed inwardly (such as by an operator's thumb) via its actuation flange 56, as best illustrated in FIG. 6, biasing tangs 58 will in turn compress springs 47, thereby increasing the outward bias of coupler blade 50. Upon release of actuation flange 56, the biasing force will tend to immediately return coupler blade to its initial or engaged position, thereby automatically gripping an endoscopic eyepiece which has been placed within alignment recess 28.

As best shown in FIGS. 6 and 7, in order to quickly couple an endoscopic ocular 15 within a coupling assembly 10 made in accordance herewith, coupler blade 50 is displaced relative seat 20 by inward pressure on actuation flange 56. Reciprocation of blade 50 along axis A also acts to move gripping jaws 60 inwardly as shown to their "release" position as illustrated in FIG. 6. In such release position, engagement lips 64 and, preferably, portions of flanges 63 are longitudinally moved to a position substantially outside the effective diameter of alignment recess 28. In this way, substantially unencumbered access to alignment recess 28 is provided for insertion of the proximal end 16 of an endoscopic ocular.

As indicated, upon placement of proximal end 16 of an endoscopic ocular 15 within the confines of the semicircular stationary guidewalls (e.g. 25 and 26), the circular flange 17 of ocular 15 is generally and preliminarily aligned with aperture 22 within recess 28. It is contemplated that the effective diameter of alignment recess 28 defined by two or more stationary guidewalls, such as guidewalls 25 and 26, will be slightly larger than the outside diameter of commonly available circular ocular flanges 17 to enable and facilitate initial alignment and insertion of flange 17 and to permit flange 17 to clear the inner edges of retaining lip 27 of guidewall 26.

Particularly, as will be understood, once inward radial pressure on actuation flange 56 of blade 50 is released, blade 50 and its attendant gripping jaw or jaws 60 will be moved outwardly along central axis A by the biasing action of springs 47. As blade 50 and its gripping jaws move in an outward direction to return to their original engagement position, engagement lips 64 of jaws 60 will engage respective portions of the angled or conical rear face 18 of circular flange 17 of ocular 15. Retainer flanges 63 may extend radially inwardly from inner surfaces 61 at a non-normal orientation to more closely correspond with the angled configuration of the conical rear faces (e.g. 18) of typical endoscopic eyepieces, as desired, and/or such angles can be accommodated by the tapered surface 66 of lip 64. In this way, gripping jaw 60 can simultaneously provide gripping forces both in a radially inward direction and in a rearward or inward direction toward ocular mounting surface 21.

It should be noted that when in engagement with ocular 15, jaws 60 provide an exceptionally secure clamping arrangement, as manipulation of the endoscope does not tend to move blade 50 toward its release position. In fact, while jaws 60 must be moved in a direction parallel to mounting surface 21 for reciprocation to release position, forces imposed by endoscope manipulation tend to act outwardly on jaws 60 perpendicularly away from mounting surface 21. Consequently, accidental release of the ocular during use is highly unlikely even if the coupling assembly/ocular combination is subjected to rough handling.

Additionally, the outward spring bias action tends to force the clamped ocular 15 in a direction toward stationary guide wall 26 as well, moving the lowermost edge circular flange 17 to a position under retention lip 27. Obviously, the "upward"/"downward" relationship of movement is merely relative to the orientation of coupling assembly 10 itself, and this description is based upon the specific orientation shown in the drawings solely for purposes of providing an example of how to use the invention. It is contemplated that coupling assembly 10 will preferably be attached to a focusing device or adapter 12 such that orientation of its actuation flange 56 in an upright or vertical position will indicate when the camera is also in an upright condition. This can be assured by providing means for attaching assembly 10 to an adapter such that flange 56 is initially properly lined up with the camera imager. In this way, a user will always know how the endoscopic device and camera are oriented.

In a preferred embodiment, the combination of the pair of inwardly disposed retainer flanges 63 and the radially inwardly extending retainer lip 27 provides a reliable three-point coupling or containment system for securely holding an endoscopic ocular 15 substantially adjacent ocular mounting surface 21. Similarly, engagement lips 64 and guidewall 26 with its retainer flange 27 prevent substantial axial movement along axis A. The engagement position of gripping jaws 60 are illustrated in FIG. 7.

It should be further noted that while the structure of coupling assembly 10 provides a stable and reliable mounting and coupling of ocular 15 as described, the biasing strength of springs 47 can be predetermined to permit the endoscope to be rotated relative to coupling assembly 10 if desired. For applications where relative rotation is undesirable, it is contemplated that additional means for preventing such rotation (e.g. set screw 36, shown with a knurled knob to facilitate tactile manipulation) can also be provided.

The quick-release of an ocular 15 clamped by the present assembly can be accomplished simply by axially moving blade 50 inwardly to its release position (FIG. 6) by engagement of actuation flange 56. Because of the relatively open nature of the coupling assembly 10 shown and described herein, substantially unencumbered visual and physical access to alignment recess 28 is provided to facilitate insertion and removal of endoscopic oculars during actual endoscopic procedures, and to simplify and increase the efficiency of cleaning and maintenance procedures.

Figure 8:
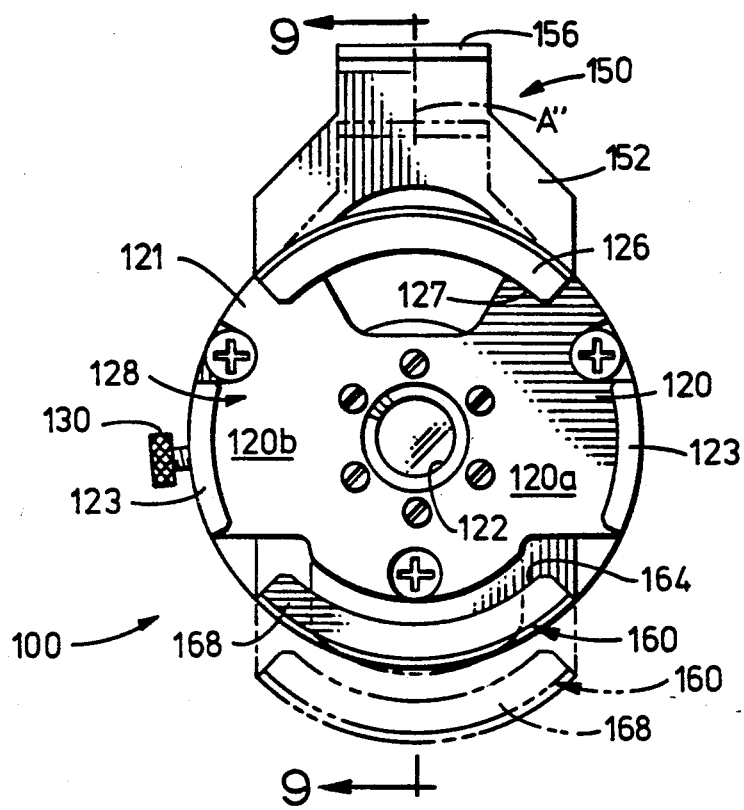
FIG. 8 is a front elevational view of an alternate preferred embodiment of a quick-release endoscopic coupling assembly made in accordance herewith, illustrating its coupler blade in release position in phantom.

FIG. 8 illustrates an alternate preferred embodiment of a coupling assembly 100, wherein a single gripping jaw 160 is attached adjacent the upper end of blade 150 for axial reciprocation along axis A". As illustrated, coupling assembly 100 comprises substantially the same arrangement as described above for coupling assembly 10, however, a single gripping jaw 160 has been substituted for the oppositely disposed pair of gripping jaws 60.

It is also contemplated that a plurality of semi-circular stationary guidewalls 123 and 126 would preferably be radially spaced about and substantially concentric with aperture 122 to define an alignment recess 128. Coupler seat 120 is illustrated as including a pair of oppositely disposed radial spokes 120a and 120b forming a substantially planar ocular mounting surface 121 about the periphery of which is formed the outwardly extending, oppositely disposed, side guidewalls 123, and lower guidewall 126 having a retaining lip 127 as described above (e.g. lip 27). Side guidewalls 123 are also illustrated as including at least one set screw 130 for applications where relative rotation between a coupled endoscopic ocular and coupling assembly 100 is not desired.

Figure 9:
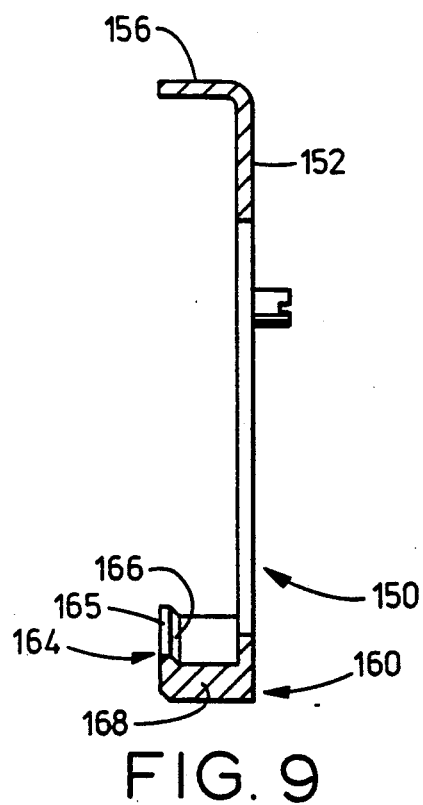
FIG. 9 is a cross-sectional view of the coupler blade of FIG. 8, taken along line 9—9 thereof.

Coupler blade 150 is shown as being arranged for axial movement along axis A" similar to that described above for blade 50. Coupler blade 150, however, is formed with a single curved or semi-circular gripping jaw 160 formed of a structure substantially similar to the outwardly extending lower guidewall 26 as described above with regard to assembly 10. Accordingly, an outwardly extending, angular engagement lip 164 and its tapered surface 166 of gripping jaw 160 would be provided along the inner edge of a semi-circular flange 168. FIG. 9 shows a cross-sectional view of coupler blade 150 and its semi-circular gripping jaw 160.

Gripping and release of an endoscopic ocular would be accomplished in a manner substantially identical to that described above with regard to coupling assembly 10, wherein the semi-circular guidewalls 123 and 126 would provide for preliminary alignment of an ocular within recess 128. Upon release of inward pressure on actuation flange 156, blade 150 and its gripping jaw 160 would be urged outwardly by a biasing means as described above. Such outward movement would cause the engagement lip 164 to contact the upper periphery of an endoscopic ocular within recess 128, and would serve to retain the clamped ocular substantially adjacent to mounting surface 121. It is contemplated that retainer lip 127 preferably extend radially inwardly a sufficient distance to ensure that when in engagement position, lips 127 and 164 are closely adjacent and preferably in contact with portions of the conical rear face of a clamped endoscopic ocular.

Once clamped within coupling assembly 100, set screw 130 may be utilized to prevent relative rotation of the ocular and assembly 100. Again, the substantially open structure of assembly 100 provides for convenient quick-release and coupling characteristics while providing essentially unencumbered visual and physical access to recess 128 for coupling, cleaning and maintenance procedures. It should be noted that such visual access also facilitates verification that an ocular is firmly and safely held in place by the coupling mechanism. Verification of secure attachment is critical to avoiding accidental decoupling which can interrupt surgical procedures, damage the equipment, and compromise the safety of the patient and staff as well.

Having shown and described the preferred embodiments of the present invention, further adaptions of the quick-release coupling assembly described herein can be accomplished by appropriate modifications by one of ordinary skill in the art without departing from the scope of the present invention. Several of such potential modifications have been mentioned, and others will be apparent to those of ordinary skill in the art. Accordingly, the scope of the present invention should be considered in terms of the following claims and is understood not to be limited to the details of structure and operation shown and described in the specification and drawings.

We claim:

1. A quick-release coupling assembly for an endoscopic ocular having a proximal end, said assembly comprising:
    an ocular mounting surface having an aperture and a longitudinal axis passing through said aperture;
    a stationary guidewall radially spaced from said aperture, said guidewall extending outwardly from said mounting surface and at least partially defining an alignment recess adjacent said mounting surface about said aperture for receiving the proximal end of an endoscopic ocular; and
    at least one gripping jaw reciprocable substantially parallel to said axis and having a clamping position and a release position, said jaw comprising an inner tab extending outwardly from said mounting surface and an engagement surface angularly disposed relative said axis and extending radially inwardly from said tab, whereby when reciprocated to said release position said engagement surface of said jaw is axially moved substantially outside of said alignment recess, and when reciprocated to said clamping position, said jaw can engage a portion of the proximal end of an ocular received within said alignment recess to effectively clamp the ocular therewithin.

2. The quick-release coupling assembly of claim 1, further comprising a pair of spaced gripping jaws reciprocable along said axis between said engagement and release positions.

3. The quick-release coupling assembly of claim 1, further comprising a pair of oppositely disposed guidewalls defining at least a portion of a generally circular alignment recess adjacent said mounting surface.

4. The quick-release coupling assembly of claim 3, wherein one of said guidewalls includes a retention lip extending radially inwardly.

5. The quick-release coupling assembly of claim 1, said assembly further comprising a means for normally biasing said gripping jaw toward said engagement position.

6. The quick-release assembly of claim 5, wherein said biasing means comprises a spring device.

7. The quick-release assembly of claim 1, said assembly further comprising a coupler seat comprising said ocular mounting surface and supporting said stationary guidewall.

8. The quick-release coupling assembly of claim 7, wherein said seat further comprises a substantially skeletal arrangement having a plurality of radially extending spoke-like elements.

9. The quick-release coupling assembly of claim 1, further comprising a longitudinally reciprocable blade member, said gripping jaw being attached to said blade member for axial reciprocation therewith.

10. The quick-release assembly of claim 1, said assembly further comprising a coupler seat comprising said ocular mounting surface and supporting said stationary guidewall and an axially reciprocable blade member, said gripping jaw being attached to said blade member for reciprocation therewith.

11. The quick-release coupling assembly of claim 1, wherein said engagement surface further comprises a tapered lip for accommodating a variety of endoscopic eyepieces.

12. A quick-release coupling assembly for an endoscopic ocular having a proximal end, said assembly comprising:
    a coupler seat having a longitudinal ocular mounting surface with an aperture and an axis passing through said aperture;
    at least one semi-circular stationary guidewall extending outwardly from said coupler seat and radially spaced from said aperture, said guidewall at least partially encircling said aperture and defining at least a portion of an alignment recess adjacent said mounting surface for receiving the proximal end of an endoscopic ocular; and
    a coupler blade member reciprocable relative to said seat and parallel to said axis, said blade further comprising at least one gripping jaw having an inner tab extending outwardly from said mounting surface, a retainer flange, attached to said tab and extending radially inwardly therefrom, and an engagement surface associated with said flange said blade having an engagement position wherein said gripping jaw may engage and grip the proximal end of an endoscopic ocular situated within said alignment recess, and a release position wherein said engagement surface is reciprocated to a position substantially outside of said alignment recess.

13. The quick-release coupling assembly of claim 12, said assembly further comprising a means for normally biasing said gripping jaw toward said engagement position.

14. The quick-release assembly of claim 12, wherein said seat further comprises a substantially skeletal arrangement having a plurality of radially extending spoke-like elements.

15. The quick-release assembly of claim 12, wherein said gripping jaw is located adjacent the upper portion of said blade member, and wherein said guidewall of said seat if substantially oppositely disposed relative to said gripping jaw along said axis.

16. The quick-release coupling assembly of claim 12, wherein said coupler blade further comprises a pair of spaced gripping jaws reciprocable along a direction parallel to said axis between said engagement and release positions.

17. The quick-release coupling assembly of claim 15, further comprising a pair of oppositely disposed additional stationary guidewall structures extending outwardly from said mounting surface and spaced radially from and substantially concentric with said alignment recess for receiving and aligning the proximal end of said endoscopic ocular.

18. The quick release coupling assembly of claim 12, wherein said seat and said blade member both comprise substantially open skeletal overall structures to facilitate drainage of fluids therethrough and to provide a lighter weight overall coupling assembly.

19. The quick release coupling assembly of claim 12, wherein said engagement surface of said gripping jaw further comprises a tapered lip to accommodate a variety of endoscopic ocular sizes and shapes.

20. A quick-release coupling assembly for an endoscopic ocular having a generally circular eyepiece with an angled attachment surface, said assembly comprising:
a coupler seat having an ocular mounting surface with an aperture and a longitudinal axis passing through said aperture along said mounting surface, said seat comprising a substantially skeletal arrangement having a plurality of radially extending spoke-like elements;
at least one stationary guidewall extending outwardly from said coupler seat and radially spaced from said aperture, said guidewall at least partially encircling said aperture and defining at least a portion of an alignment recess adjacent said mounting surface for preliminarily aligning an endoscopic eyepiece to be coupled; and
a coupler blade member reciprocably mounted relative to said seat for selective movement parallel to said axis, said blade further comprising a pair of spaced eyepiece gripping jaws, each said jaw having an inner tab extending outwardly from said blade member and away from said mounting surface, a retainer flange having proximal and distal ends and being attached at its proximal end to said tab and extending radially inwardly therefrom toward said aperture, and an eyepiece engagement surface located adjacent said distal end of said flange, said blade having an engagement position wherein said gripping jaws may engage and grip the proximal end of an endoscopic ocular situated within said alignment recess, and a release position wherein said engagement surfaces of said jaws are reciprocated to a position outside of said alignment recess.

21. The quick release coupling assembly of claim 20, wherein said engagement surface of at least one of said gripping jaws further comprises a tapered lip to accommodate a variety of endoscopic eyepiece sizes and shapes.

* * * * *

UNITED STATES PATENT AND TRADEMARK OFFICE
CERTIFICATE OF CORRECTION

PATENT NO. : 5,205,280
DATED : April 27, 1993
INVENTOR(S) : Allan G. Dennison & Larry E. Shepherd It is certified that error appears in the above—identified patent and that said Letters Patent is hereby corrected as shown below:

In column 12, claim 12, line 33, delete "a longitudinal" and insert --an--

In column 12, claim 12, line 34, delete "an" and insert --a longitudinal--

In column 12, claim 12, line 49, insert "," after --said flange--

In column 12, claim 15, line 67, delete "if" and insert --is--

In column 12, claim 12, line 47, after "retainer flange" delete --,--

Signed and Sealed this

Fifteenth Day of February, 1994

Attest:

BRUCE LEHMAN

Attesting Officer

Commissioner of Patents and Trademarks